(12) United States Patent
Ferrone et al.

(10) Patent No.: US 7,887,822 B2
(45) Date of Patent: Feb. 15, 2011

(54) PEPTIDES FOR STIMULATING AN IMMUNE RESPONSE AGAINST MELANOMA

(75) Inventors: Soldano Ferrone, Buffalo, NY (US); Chien-Chung Chang, Taipei (TW); Wei Luo, Getzville, NY (US); Xinhui Wang, Williamsville, NY (US); Debashis Ghosh, Getzville, NY (US)

(73) Assignees: Health Research, Inc., Buffalo, NY (US); Hauptman-Woodward Medical Research Institute, Buffalo, NY (US)

( * ) Notice: Subject to any disclaimer, the term of this patent is extended or adjusted under 35 U.S.C. 154(b) by 1233 days.

(21) Appl. No.: 11/487,877

(22) Filed: Jul. 17, 2006

(65) Prior Publication Data

US 2007/0190061 A1    Aug. 16, 2007

Related U.S. Application Data

(60) Provisional application No. 60/751,541, filed on Dec. 16, 2005, provisional application No. 60/753,532, filed on Dec. 23, 2005.

(51) Int. Cl.
*A61K 39/00* (2006.01)
(52) U.S. Cl. .................................. 424/277.1; 530/300
(58) Field of Classification Search ........................ None
See application file for complete search history.

(56) References Cited

U.S. PATENT DOCUMENTS 5,866,124 A * 2/1999 Hardman et al. ......... 424/131.1

OTHER PUBLICATIONS

Gerd Pluschke, et al. Molecular cloning of a human melanoma-associated chondroitin sulfate proteoglycan, Proc. Natl. Acad. Sci. USA vol. 93, pp. 9710-9715, Sep. 1996.

Chen ZJ, et al. Human high molecular weight melanoma—associated antigen mimicry by mouse antiidiotypic monoclonal antibody MK2-23. Characterization of the immunogenicity in syngeneic hosts. J Immunol. Aug. 1, 1991; 147(3):1082-91. (Abstract).

Kusama M, et al. Characterization of syngeneic antiidiotypic monoclonal antibodies to murine anti-human high molecular weight melanoma—associated antigen monclonal antibodies. J Immunol. Dec. 1, 1989; 143(11):3844-52. (Abstract).

Eike Staub, et al. A novel repeat in the melanoma-associated chondroitin sulfate proteglycan de¢nes a new protein family. FEBS Letters 527 (2002) 114-118.

* cited by examiner

*Primary Examiner*—Michael Pak
(74) *Attorney, Agent, or Firm*—Hodgson Russ LLP

(57) ABSTRACT

Provided in the present invention are recombinant peptides and a method for using the peptides in stimulating an immune response against human high molecular weight-melanoma associated antigen (HMW-MAA). The peptides were designed from the identification of regions of structural and amino acid sequence homology between HMW-MAA and the mouse anti-idiotypic monoclonal antibody MK2-23. The method comprises the step of administering to an individual a peptide of the invention in an amount effective to elicit an immune response against HMW-MAA.

18 Claims, 5 Drawing Sheets

PEPTIDES FOR STIMULATING AN IMMUNE RESPONSE AGAINST MELANOMA

This application claims priority to U.S. provisional application Ser. No. 60/751,541, filed Dec. 16, 2005, and to U.S. provisional application Ser. No. 60/753,532, filed Dec. 23, 2005, the disclosures of which are incorporated herein by reference.

FIELD OF THE INVENTION

The present invention is generally directed to cancer therapy and more particularly to peptides for use in eliciting an immune response against melanoma.

BACKGROUND OF THE INVENTION

Melanomas are aggressive, frequently metastatic tumors derived from either melanocytes or melanocyte related nevus cells ("Cellular and Molecular Immunology" (1991) (eds) Abbas A. K., Lechtman, A. H., Pober, J. S.; W. B. Saunders Company, Philadelphia: pages 340-341). According to the American Cancer Society, melanomas make up approximately three percent of all skin cancers but cause most skin cancer-related deaths, and the incidence rate for melanoma (number of new cases of melanoma per 100,000 people each year) has more than doubled since 1973. While the mortality rate for melanoma has increased at a slower pace, there is an ongoing need to develop new melanoma therapies.

Like many cancers, melanomas are believed to arise at least in part because of unresponsiveness to self-tumor antigens which prevents the immune system from eliminating cancerous cells. One technique that has been investigated to overcome such unresponsiveness is the use of antigen mimics. Various types of tumor antigen mimics have been identified. Among them, the most extensively utilized antigen mimics are anti-idiotypic antibodies (anti-Id-Abs), which have been developed in several human tumor antigen systems (for review, see Wang, et al. (2001) Cancer Chemother. Biol. Response Modif. 19, 309-326).

Anti-id mAbs markedly differ in their immunogenicity as measured by their ability to elicit a humoral immune response to the corresponding self-tumor antigen. However, the cause of this variability is not known. This lack of information reflects the limited knowledge about the structural basis of antigen mimicry by anti-id antibodies and about the ability of a mimic to overcome unresponsiveness to a self-tumor antigen.

For example, an anti-id mAb (MK2-23) has been developed against a melanoma antigen (Kusama et al. (1989) J. Immunol. 143, 3844-3852). However, little is known about the molecular mimicry of the antigen by this anti-id mA. This lack of information has precluded further development of compositions based on this mimicry for use in stimulating an immune response to melanomas. Therefore, there is a need to analyze the molecular basis of melanoma antigen mimicry by this anti-id mAb and to develop compositions based on the analysis for use in stimulating an immune response to melanoma.

SUMMARY OF THE INVENTION

The present invention provides recombinant peptides for use in stimulating an immune response against melanoma. The peptides were designed from regions of structural and amino acid sequence homology identified herein between HMW-MAA and the mouse anti-idiotypic monoclonal antibody (anti-id mAb) MK2-23, which mimics an HMW-MAA epitope. In particular, X-ray crystallography analysis of the Fab' portion of MK2-23 was used to identify regions of the heavy and light chains of the MK2-23 anti-idiotypic antibody which displayed similar folding patterns as the region of the HMW-MAA comprising the epitope mimicked by MK2-23. These studies indicated that the complementarity determining region 3 (CDR3) of its heavy chain (also referred to herein as "H3") and the complimentarity determining region 1 (CDR1) of its light chain (also referred to herein as "L1") display partial amino acid sequence homology and a similar structural folding as a portion of the HMW-MAA protein that comprises the epitope which is mimicked by MK2-23. Based on these data, three peptides are provided—one each from the H3 and the L1 region of MK2-23 and one from the HMW-MAA.

The present invention also provides a method for using the peptides identified herein for stimulating an immune response in an individual against melanoma. The method comprises administering to the individual an amount of a composition comprising one or more peptides of the invention in an amount effective to stimulate an immune response against HMW-MAA.

BRIEF DESCRIPTION OF THE DRAWINGS

In FIG. 2A, the CDR loops of the light (CDR1L) (L1) (green) and heavy (CDR3H) (H3) (yellow) chains are shown as labeled. The boxed area is shown in stereo images (FIG. 2B), detailing the secondary and tertiary structures of anti-id mAb MK2-23 L1 and H3 and their final electron density maps. Hydrogen bonds are shown by dotted lines

DETAILED DESCRIPTION OF THE INVENTION

The present invention provides peptides for use in stimulating an immune response to HMW-MAA. The peptides were identified by analyzing the structural basis of HMW-MAA mimicry by the anti-id mAb MK2-23. This analysis entailed determining the amino acid sequence and solving the three-dimensional structure of the Fab' fragment of MK2-23 and comparing this information with the amino acid sequence and predicted structure of HMW-MAA. Based on this analysis, sequence and structural homology between a putative epitope on HMW-MAA and the portion of MK2-23 that is believed to mimic the epitope was determined and used to design the peptides. These peptides are designated as "PMK2-23H3" (ARSNYVGYHVRWYFD; SEQ ID NO:1); "PMK2-23L1" (SVEYYGSSLMQ; SEQ ID NO:2) and "PHMW-MAA.D2.7" (IRSGDEVHYHV TAGPRW; SEQ ID NO:3).

Figure 1:
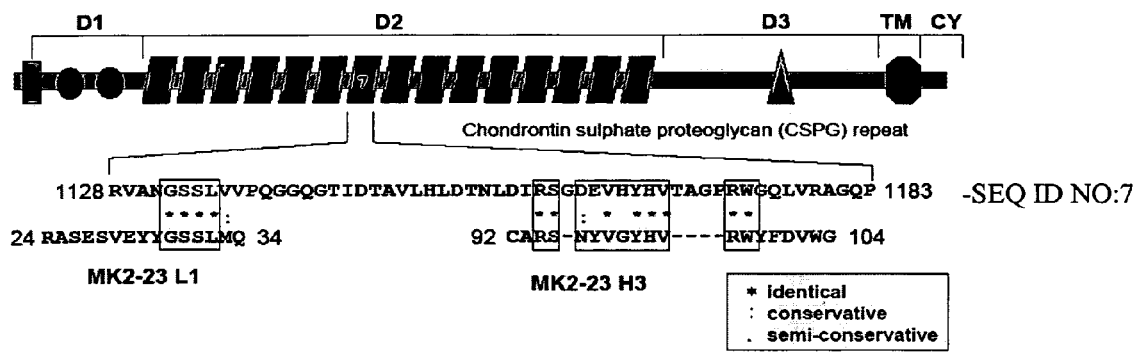
FIG. 1 is a graphical depiction of the partial sequence homology and structural similarity between the HMW-MAA putative chondroitin sulfate proteoglycan (CSPG) repeat (HMW-MAA.D2.7) and anti-id mAb MK2-23 L1 and H3 loops. The putative domain organization of HMW-MAA is illustrated according to Staub et al. (Staub, et al. (2002) FEBS Lett. 527, 114-118). The numbering of anti-id mAb MK2-23 L1 and H3 follows the Kabat convention (Kabat, et al. (1991) Sequences of Proteins of Immunological Interest (Public Health Service, National Institutes of Health, Washington, D.C.; 5th Ed). There are 15 CSPG repeat units (filled trapezoid) located in domain 2 of HMWMAA. The predicted β-strand structures of HMWMAA. D2.7 are underlined. The homologous regions are boxed. The residues in anti-id mAb MK2-23 L1 and H3 that show 100% identity with the HMW-MAA residues are designated by an asterisk. Conservative changes are designated by two vertical dots. The alignment was performed with the ClustalW program (European Bioinformatics Institute). Abbreviations: D, domain; TM, transmembrane; CY, cytoplasmic tail.

In particular, and as shown in FIG. 1, the amino acid sequence of peptide PMK2-23H3 is identical to the amino acid sequence of a portion of the H3 loop of anti-id mAb MK2-23 that has partial homology to HMW-MAA. The amino acid sequence of the PMK2-23L1 peptide is identical to the amino acid sequence of a portion of the L1 loop of anti-id mAb MK2-23 that has partial homology to HMW-MAA. PHMW-MAA.D2.7 has an amino acid sequence that is identical to a region of HMW-MAA that has partial homology to the H3 loop of anti-id mAb MK2-23.

The MK2-23 anti-id mAb was derived from a mouse immunized with the HMW-MAA-specific idiotypic mAb 763.74 Kusama, et al. (1989) J. Immunol. 143, 3844-3852. Anti-id mAb MK2-23 and idiotypic mAb 763.74 are described in U.S. Pat. No. 5,493,009. The nucleotide and protein sequences for the anti-id mAb MK2-23 light and heavy chain variable regions have been deposited in the GenBank database under GenBank Accession Numbers DQ241816 (Dec. 13, 2005 entry) and DQ241817 (Dec. 13, 2005 entry), respectively.

The three-dimensional (3D) structure of the Fab' portion MK2-23 is disclosed herein. The atomic coordinates and structure factors are available in the Protein Data Bank (PDB), Research Collaboratory for Structural Bioinformatics, Rutgers University, New Brunswick, N.J. (http://www.rcsb.org/) under PDB # 2AAB.

The 3D structure of the Fab' portion of MK2-23 shows that the MK2-23 CDR3 region of its heavy chain (H3) and its light chain CDR1 (L1) are in close proximity. These regions display partial amino acid sequence homology with MHW-MAA as shown in FIG. 1. Further, these regions display similar structural folding similar to that of the HMW-MAA protein. Thus, and without intending to be bound by any particular theory, it is believed that the CDR3 and CDR1 regions of MK2-23 which display homology with HMW-MAA are the source of HMW-MAA mimicry by MK2-23. Accordingly, the present invention provides peptides designed from a region of amino acid sequence and structural homology between MK2-23 and HMW-MAA. Binding data demonstrate that the PMK2-23H3 peptide competes with PHMW-MAA.D2.7 for binding to mAb 763.74 (against which the anti-id mAb MK2-23 was raised). Data presented herein also demonstrate that administration of PMK2-23H3 to animals stimulates the production of antibodies which bind to cells expressing HMW-MAA, indicating that this peptide stimulates an immune response that could overcome self-unresponsiveness to melanoma.

The peptides of the invention can be prepared by any technique known to those skilled in the art or those later developed, such as by recombinant genetic techniques or by chemical synthesis. For example, peptides can be prepared using the solid-phase synthetic technique (Merrifield, J. Am. Chem. Soc., 15:2149-2154 (1963); M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985). A summary of peptide synthesis techniques is provided in J. Stuart and J. D. Young, Solid Phase Peptide Synthesis, Pierce Chemical Company, Rockford, Ill. (1984). The synthesis of peptides by solution methods may also be used, as described in *The Proteins*, Vol. II, 3d Ed., p. 105-237, Neurath, H., et al., Eds., Academic Press, New York, N.Y. (1976).

In general, the synthesis of the peptides involves the sequential addition of one or more amino acid residues or suitable protected amino acid residues to a growing peptide chain. Typically, the carboxyl group of the first amino acid residue is pre-attached to a solid support, the amino group being protected by a first, selectively-removable protecting group. A second, different, selectively removable protecting group is utilized with amino acids containing a reactive side group, such as lysine. After the removal of the first protecting group, the carboxyl group of the second amino acid is coupled to the amino group of the first amino acid. The process is then repeated until the peptide is complete, at which time the peptide is removed from the solid support and purified. The synthesized peptides may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing using standard techniques.

The peptides of the invention may be coupled with various conventional moieties to impart desired characteristics, such as improved solubility or immunogenicity. Moieties that can improve the solubility, absorption, biological half life, and the like, or attenuate undesirable side effects can be found in Remington's Pharmaceutical Sciences (18th Edition, A. R. Gennaro et al. Eds., Mack Publishing Co., Easton, Pa., 1990). The peptides may also be conjugated using standard techniques to moieties intended to enhance the immune response stimulated by the peptides. For example, the peptides may conjugated to one or more soluble immunogenic macromolecular carriers, such as serum albumin, keyhole limpet hemocyanin, or dextran. T helper peptides, cytokines or adjuvants can also be utilized to improve immunogenicity. Additional conjugates suitable for improving the efficacy of the peptides include targeting agents, such as antibodies or receptor ligands, and stabilizing agents, such as lipids.

It will be understood by those skilled in the art that routine modifications to the peptide amino acid sequences, such as conservative amino acid substitutions, that will not affect the function of the peptides are within the purview of those skilled in the art.

In one embodiment, one or more peptides of the invention may be combined with pharmaceutically acceptable carriers to form compositions for use in stimulating an immune response to HMW-MAA in an individual. Acceptable pharmaceutical carriers for use with proteins are described in Remington's Pharmaceutical Sciences (18th Edition, A. R. Gennaro et al. Eds., Mack Publishing Co., Easton, Pa., 1990). It will be recognized by one of skill in the art that the form and character of the pharmaceutically acceptable carrier will be dictated by the amount of peptide with which it is to be combined, the route of administration and other well-known variables. Compositions comprising the peptides of the invention may additionally comprise conventional adjuvants.

The present invention also provides a method for using the peptides provided herein for stimulating an immune response in an individual against HMW-MAA. The method comprises administering to the individual a composition comprising one or more peptides of the invention in an amount effective to stimulate an immune response against HMW-MAA.

Various methods known to those skilled in the art may be used to administer compositions comprising the peptides. These methods include intradermal, intramuscular, intraperitoneal, intravenous, subcutaneous, and intranasal routes. Further, those skilled in the art will recognize that the dosage of the peptides will depend on well known variables, such as the size of the individual and the stage of the disease. For example a dose of 500 to 1,000 micrograms can be administered to individuals.

In one embodiment, a composition comprising a peptide of the invention is administered to an individual having a melanoma tumor in an effective amount such that the immune response stimulated by the peptide is effective to inhibit the growth of the melanoma.

In another embodiment, a composition comprising a peptide of the invention is administered to an individual who is in remission from a melanoma tumor in an effective amount such that the immune response stimulated by the peptide inhibits the recurrence of the melanoma.

The following Examples are meant for purposes of illustration and are not meant to limit the scope of the invention in any way.

EXAMPLE 1

This Example demonstrates the identification of sequence and structural similarities between mAb MK2-23 and HMW-MAA.

To investigate whether amino acid sequence homology plays a role in the HMW-MAA mimicry by anti-id mAb MK2-23, we compared the amino acid (a.a.) sequence of the anti-id mAb MK2-23 CDRs with that of the HMW-MAA core protein (Pluschke, et al. (1996) Proc Natl Acad Sci USA. 93, 9710-9715), since CDRs constitute the idiotope of an antibody. Only a partial homology was found between the MK2-23H3 and the HMW-MAA core protein (FIG. 1 and data not shown). This region corresponds to residues 94 to 102 within anti-id mAb MK2-23H3, displaying 8 identical, though discontinuous, and 1 conservative matches with the region spanning from residues 1159 to 1174 in the HMW-MAA core protein. In addition, the region corresponding to residues 29-33 within anti-id mAb MK2-23 L1 shows 4 identical and 1 conservative matches with residues 1132 to 1136 of the HMW-MAA core protein (FIG. 1). The two homologous regions map, with only 21 a.a. apart, to the seventh of the 15 putative CSPG repeat units of the domain 2 of HMW-MAA (designated HMW-MAA.D2.7, residues 1128 to 1216). The HMW-MAA.D2.7 segment is predicted to adopt an all-β fold conformation, comprising 8 β-strands (Staub, et al. (2002) FEBS Lett. 527, 114-118). This prediction is supported by the alignment of the putative HMW-MAA.D2.7 β-strands to the 6 β-strands of a N-cadherin fragment with a known 3-D structure (PDB code 1NCJ). Interestingly, it is disclosed herein that the two HMW-MAA.D2.7 regions (residues 1132 to 1135 and residues 1159 to 1174), with which anti-id mAb MK2-23 L1 and H3 have homology, are located within the predicted first and fourth β-strands, respectively, in the HMW-MAA segment (FIG. 1). This indicates that the anti-id mAb MK2-23 L1 and H3 loops represent the moiety that mimics the HMW-MAA epitope.

To determine whether anti-id mAb MK2-23 L1 and H3 loops display a structural fold similar to that of the HMW-MAA.D2.7 segment, we crystallized and solved the structure of the anti-id mAb MK2-23 Fab' fragments, as follows. mAb MK2-23 F(ab')$_2$ fragments were generated by digesting with immobilized pepsin (Pierce, Rockford, Ill.) mouse mAb IgG1 MK2-23 (Chen, et al. (1991) J. Immunol. 147, 1082-1090), which was purified from ascites by protein A chromatography (Bio-Rad, Hercules, Calif.). High-purity mAb MK2-23 F(ab')$_2$ fragments were obtained by sequential protein A column and S-200 gel filtration chromatography. Peak S-200 fractions were pooled and concentrated to 7.9~10 mg/ml in low salt phosphate buffer (50 mM KH$_2$PO4, 10 mM NaCl, pH 7.4). Purified F(ab')$_2$ fragment preparations were pre-incubated at room temperature with 5 mM dithiothreitol at pH 5.5 for 1.5 hrs, yielding monomeric Fab' fragments.

Diffraction-quality crystals were obtained from 20% polyethylene glycol 6000, in 0.1M HEPES buffer, pH 7.5, at a protein concentration of 7.9 mg/ml. Protein and precipitant solutions were mixed at the 3:2 ratio and droplets were allowed to vapor diffuse against wells of precipitant solutions in hanging droplets. Fab' fragments were crystallized in the orthorhombic space group P2$_1$2$_1$2$_1$ having unit-cell dimensions a=75.05 Å, b=76.89 Å, c=82.18 Å, α=β=γ=90' and one Fab' molecule in the asymmetric unit. Diffraction data to 2.50 Å resolution were collected with a crystal flash frozen in liquid nitrogen on a R-AXIS IV area detector equipped with a rotating anode X-ray source (93266 measured intensities, 17003 unique reflections, 99.9% complete, Intensity/σ(Intensity)=4.2 in the highest resolution shell, Rmerge=0.067).

The 3-D structure of the mAb MK2-23 Fab' fragments was determined by the molecular replacement method using a known Fab structure (Protein Data Bank code: 2RCS) as the search model and XPLOR routines (Brünger, et al. (1992) X-PLOR: A System for X-ray Crystallography and NMR. Yale University Press, New Haven, Conn.). The experimentally determined sequences for the variable domains were built into the electron density and the model was subjected to several rounds of refinement and rebuilding using the CNS package of software (Brünger, et al. (1998) Acta Crystallogr. D Biol Crystallogr. 54, 905-921). The final crystallographic R factor for 441 residues and 66 water molecules (3444 total atoms) is 0.236 with an R-free value of 0.297 for 16656 reflections between 33 and 2.50 Å resolution. Table 1 provides a summary of data collection and structure refinement results.

TABLE 1

| | |
|---|---|
| Total reflections measured (Cu K$_\alpha$ radiation, $\lambda$ = 1.5418 Å) | 93465 |
| Unique number of reflections | 17003 |
| Resolution range | 33-2.50 Å |
| Intensity/σ(Intensity) in the highest shell (2.59-2.50 Å) | 4.2 |
| Percent of possible reflections measured (highest shell) | 99.7 (99.8) |
| R$_{merge}$(Intensity) (highest shell) | 0.067 (0.327) |
| Non-hydrogen protein atoms in the model (441 amino acids: 217 in L and 224 in H) | 3378 |
| Solvent water oxygen atoms included | 66 |
| Unique reflections used for refinement | 16656 |
| (Percent of possible) | (98%) |
| Crystallographic R-factor | 0.236 |
| Free R-value | 0.297 |
| (Free R test set size) | (4.9%) |
| RMS deviation from ideal values: | |
| Bond length (Å) | 0.007 |
| Bond angle (°) | 1.5 |
| Dihedral angle (°) | 26.8 |
| Estimated coordinate error: | |
| From Luzzati plot (Å) | 0.34 |
| From SIGMAA (Å) | 0.31 |
| Temperature factor (B) from Wilson plot (Å$^2$) | 45.8 |
| Mean atomic B factor (Å$^2$) | 35.6 |
| Ramachandran plot: | |
| Non-glycine and non-proline residues | 379 |
| Residues in the allowed ranges | 377 |
| Residues in the disallowed ranges | 2 |

Figure 2A:
FIGS. 2A and 2B are graphical representations of the crystal structure of anti-id mAb MK2-23 Fab' fragment at 2.5 Å resolution shown in a ribbon diagram.

The overall structure of anti-id mAb MK2-23 Fab' fragment exhibits the typical immunoglobulin fold with 377 of 379 non-Gly and non-Pro residues in the allowed regions (FIG. 2A & Table 1). The two residues that are in the disallowed region are Ala51 of the L chain and Ser172 of the H chain, both of which are located on turns with well-defined electron densities. Our experimental electron densities agree well with the deduced amino acid sequences of anti-id mAb MK2-23 Fab' L and H chains, except for the following discrepancies. An Ala side chain was better accommodated than an Arg at residue 71 of the H chain. A few solvent-exposed side chains, such as Tyr100 and Arg100C of the H chain (on the H3 loop), did not show appreciable electron densities. It is likely that these side chains participate in antigen recognition and are dynamically disordered in absence of an antigen.

Next the structural features of L1 and H3 loops of the anti-id mAb MK2-23 were examined. L1 consists of residues Arg$^{24}$, Ala$^{25}$, Ser$^{26}$, Glu$^{27}$, Ser$^{27A}$, Val$^{27B}$, Glu$^{27C}$, Tyr$^{27D}$, Tyr$^{28}$, Gly$^{29}$, Ser$^{30}$, Ser$^{31}$, Leu$^{32}$, Met$^{33}$ and Gln$^{34}$ (SEQ ID NO:5) (Kabat, et al. (1991) Sequences of Proteins of Immunological Interest (Public Health Service, National Institutes of Health, Washington, D.C.; 5th Ed). According to current classifications (Al-Lazikani, et al. (1997) J. Mol. Biol. 273, 927-948), anti-id mAb MK2-23 L1 belongs to the V$_k$ L1 canonical structure 5, containing 4 insertions. An interesting feature of this L1 loop is the formation of a pair of anti-parallel strands linked by three inter-strand hydrogen bonds (27BCO-HN32, 27DNH-OC30 and 27DCO-HN30) and a left-handed hairpin turn having Tyr28 and Gly29 backbones in the (+,+) helical conformational space of the Ramachandran plot.

The H3 loop, consisting of residues Ser$^{95}$, Asn$^{96}$, Tyr$^{97}$, Val$^{98}$, Gly$^{99}$, Tyr$^{100}$, His$^{100A}$, Val$^{100B}$, Arg$^{100C}$, Trp$^{100D}$, Tyr$^{100E}$, Phe$^{100F}$, Asp$^{101}$ and Val$^{102}$, (SEQ ID NO:6) contains 6 insertions (Kabat, et al. (1991) Sequences of Proteins of Immunological Interest (Public Health Service, National Institutes of Health, Washington, D.C.; 5th Ed). H3 is relatively longer than that of other mouse immunoglobulins; it is only shorter than that of mAb R19.9 (PDB 1FAI) and mAb R45-45-11 (PDB 1IKF) by 1 and 3 residues, respectively. In accordance with the structural patterns of the immunoglobulin H3 loop torso region (Morea, et al. (1998) J. Mol. Biol. 275, 269-294), anti-id mAb MK2-23H3 belongs to a class in which the torso region does not contain a β-bulge, which is the most common class, but a regular β-sheet hairpin structure (Morea, et al. (1998) J. Mol. Biol. 275, 269-294). The salt bridge between Arg$^{94}$ and Asp$^{101}$ is absent, but like in most immunoglobulins, the combination of the length and sequence of the loop between Arg$^{94}$ and Asp$^{101}$ dictate to a large extent the specificity. The anti-parallel strands at the loop termini are held by hydrogen bonding (95CO—HN101, 96NH—OC100E, 96CO—HN100E and 98NH—OC100C). At the tip of the loop, residues Tyr100 to Arg100C form a distorted type III helical turn with a 100CO—HN100C hydrogen bond. Similar to L1, H3 also displays high thermal motion (average B ~60 Å$^2$); however, the main chain and most of the side chain electron densities, except those of Tyr97 and Arg100C, are well defined to allow an unequivocal tracing of the backbone. It is noteworthy that the L1 and H3 loops pack closely against each other through hydrophobic interactions (L1 Leu32 side chain against the H3 main chain, Val$^{106}$ and Tyr$^{27D}$ side chains) and through the formation of one hydrogen bond (L1 Gln$^{34}$ to H3 Trp$^{100DCO}$).

Figure 2B:
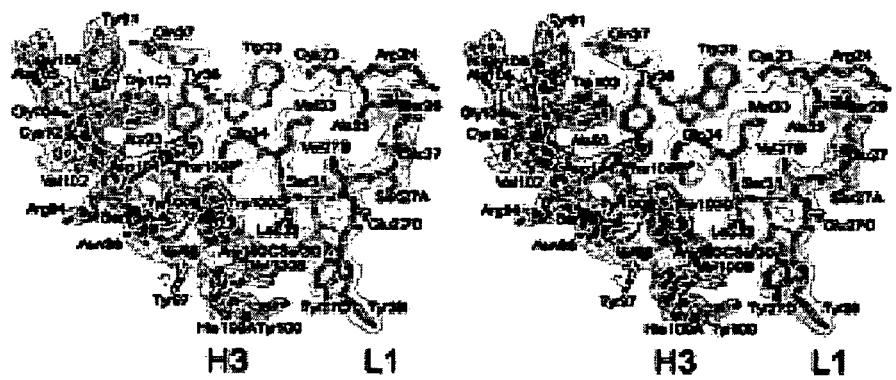

To examine the structural variation of the anti-id mAb MK2-23 L1 and H3 loops as compared to other anti-id antibodies, we aligned the 3-D structure of these two loops with those of the four anti-id mAb structures available thus far: 409.5.3 (PDB 1AIF), 6A6 (PDB 1PG7), E225 (PDB 1CIC) and E5.2 (PDB 1DVF). Two anti-anti-id mAbs, 131 (PDB 2CK0) and GH1002 (PDB 1 GHF), and two idiotypic mAb, Mopc21 (PDB 1IGC) and R24 (PDB 1R24), were used for comparison. Using least squares fitting, the loop termini, which correspond to the conserved residues 23 and 37 of the L chain, and 91 and 106 of the H chain, superimpose well with root mean squared deviations (rmsd) between 0.2 and 1 Å (data not shown). Between the termini, the loops, and especially H3, adopt varying conformations with the largest rmsd around 6.5 Å. The H3 loop of anti-id mAb MK2-23 is long and forms a pair of anti-parallel β-strands linked by four hydrogen bonds (FIG. 2B). Together with the L1 loop, the H3 loop of anti-id mAb MK2-23 projects a 41 amino acid residue long surface which is the most protruded among all the anti-id antibodies with a known three-dimensional structure.

The crystal structure of the anti-id mAb MK2-23 Fab' fragments reveals distinctive features of the 3-D conformations of CDR loops L1 and H3, strongly suggesting that the two loops play important roles in the interaction with mAb 763.74 and in the mimicry of the HMW-MAA epitope defined by mAb 763.74. Interestingly, when compared with H3 loops of anti-id mAb 409.5.3 (PDB 1AIF), 6A6 (PDB 1PG7), E225 (PDB 1CIC) and E5.2 (PDB 1DVF) with known 3-D structures, anti-id mAb MK2-23 L1 and H3 appear to be more protruded, displaying large variations in conformations. Of note is the left-handed hairpin turn present in L1 and a pair of anti-parallel β-strands with strong inter-strand hydrogen-bonding present in H3. These findings are in agreement with the predicted structure of the corresponding HMW-MAA.D2.7 fragment, which may also adopt a similar β-strand conformation (Staub, et al. (2002) FEBS Lett. 527, 114-118).

EXAMPLE 2

This Example demonstrates similarity in the in vitro reactivity of the anti-id mAb MK2-23-derived peptide and of an HMW-MAA derived peptide.

PMK2-23H3, PMK2-23L1, and PHMW-MAA.D2.7 were synthesized by N.C. Wang, Hospital for Sick Children, Toronto, ON, Canada. A synthetic peptide derived from $\beta_2$-microglobulin (Pb2m, KNGERIEKVEHS SEQ ID NO:4), used as a negative control, was purchased from University of Georgia Molecular Genetics Instrumentation Facility (Athens, Ga.). mAb 763.74 was purified from ascitic fluid by sequential ammonium sulphate and caprylic acid precipitation (Temponi, et al. (1989) Hybridoma. 8, 85-95). The purity and activity of mAb preparations were assessed by SDS-PAGE and by testing with the corresponding antigen in a binding assay, respectively. Biotinylation was performed using NHS-LC-biotin (Pierce, Rockford, Ill.) according to the manufacturer's instructions.)

Escalating concentrations of peptides were incubated with biotinylated mAb 763.74 (0.5 mg/ml) at 4° C. overnight in U-bottom 96-well plates. The mixture was then incubated with HMW-MAA-bearing melanoma cells Colo38 ($10^5$/well) for 1 h at 4° C. After three washes with 1% bovine serum albumin in phosphate buffered saline, an optimal amount of horseradish peroxidase-conjugated streptavidin was added. Reactions were then developed and visualized with the TMB substrate system (KPL, Gaithersburg, Md.). Reactions were reported as optical density (O.D.) measured with an ELISA reader. Percent inhibition was calculated by the formula: $100\% \times (O.D._{irrelevant\ peptide} - O.D._{test\ peptide})/O.D._{irrelevant\ peptide}$. Dissociation constant ($K_d$) was calculated as the molar concentration of the peptide required to cause a 50% inhibition of binding of biotinylated mAb 763.74 to HMW-MAA-bearing melanoma cells Colo38 (Temponi, et al. (1992) Cancer Res. 52, 2497-2503).

Figure 3:
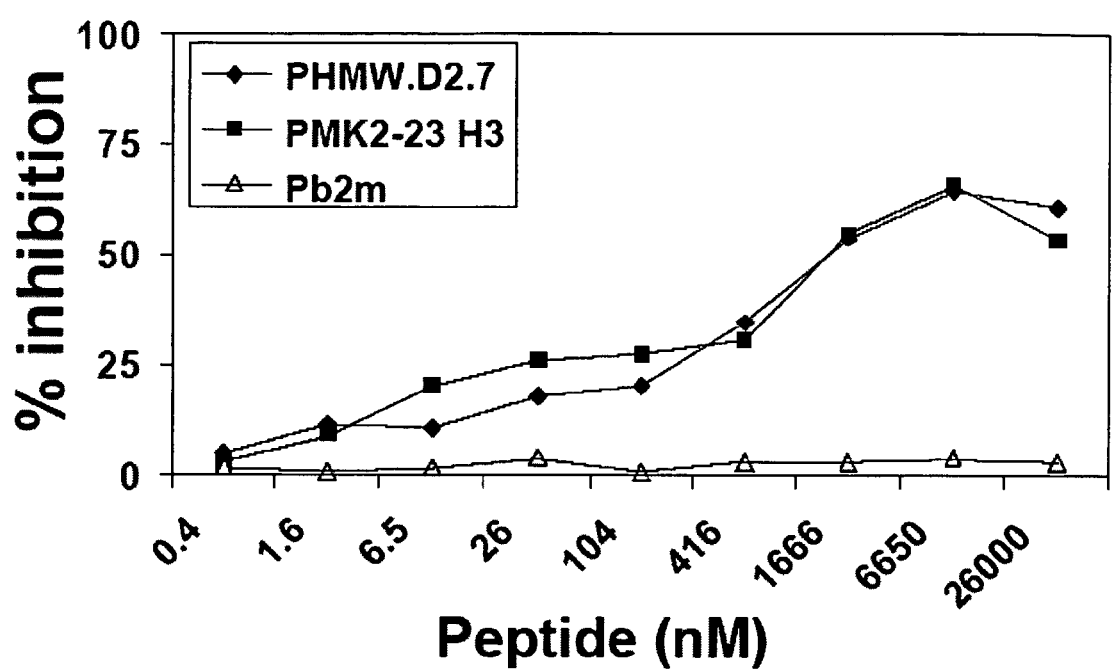
FIG. 3 is a graphical depiction of dose-dependent inhibition by anti-id mAb MK2-23H3-derived peptide PMK2-23H3 of binding of mAb 763.74 to HMW-MAA-bearing Colo38 melanoma cells. Peptides PHMW.D2.7 (HMW-MAA-derived), PMK2-23H3 (anti-id mAb MK2-23H3-derived), and an irrelevant control peptide Pb2m (β2-microglobulin-derived) at increasing concentrations were incubated with biotinylated mAb 763.74 (0.5 µg/ml) and assayed as described in Example 2. Results of one of three representative experiments are shown.

Peptide PMK2-23H3, which was based on the H3 loop of anti-id mAb MK2-23 encompassing the HMW-MAA-homologous amino acid sequence (FIG. 1) was analyzed for reactivity with the HMW-MAA-specific idiotypic mAb 763.74. As shown in FIG. 3, peptide PMK2-23H3 inhibits the binding of mAb 763.74 to HMW-MAA-bearing melanoma cells to a similar extent as the HMW-MAA.D2.7-derived peptide PHMW.D2.7. The inhibition is specific since the irrelevant peptide Pb2m had no detectable effect on the binding of mAb 763.74 to melanoma cells. The $K_d$ for peptides PMK2-23H3 and PHMW.D.2.7 is 871 nM and 900 nM, respectively. The peptide SVEYYGSSLMQ (designated as PMK2-23L1), which was derived from the L1 loop of anti-id mAb MK2-23 encompassing the described HMW-MAA-homologous a.a. sequence, was also synthesized. Because of its low solubility, peptide PMK2-23L1 could not be used alone or in combination with peptide PMK2-23H3 in peptide binding assays.

Thus, the anti-id mAb MK2-23H3-derived peptide PMK2-23H3 inhibits the binding of mAb 763.74 to HMW-MAA-bearing cells to the same extent as the corresponding HMW-MAA-derived peptide PHMW.D2.7, demonstrating the structural similarity of MK2-23H3 to an HMW-MAA antigen.

EXAMPLE 3

This Example demonstrates that peptide PMK2-23H3 elicits antibodies reactive against cells expressing HMW-MAA.

To demonstrate this effect, peptide PMK2-23H3 conjugated to the carrier protein keyhole limpet hemocyanin with the cross-linking agent m-maleimidobenzoyl-N-hydroxysuccinimide ester (Pierce) was mixed with complete Freund adjuvant for priming (100 µg/injection) and with incomplete Freund adjuvant for boosting (50 µg/injection). Immunizations were given subcutaneously to 8-week-old female BALB/c mice (obtained from Taconic Farms, Germantown, N.Y.) (5 per group) on day 0, 21, and 42. Sera were harvested before immunization and on day 7 and 28. They were tested for reactivity with the immunizing peptide coated on 96-well plates (Temponi, et al. (1989) Hybridoma. 8, 85-95) and with HMW-MAA-bearing melanoma cells in ELISA and fluorescence-activated cell sorting (FACS) analysis using conventional techniques as previously described (Chen, et al. (1991) J. Immunol. 147, 1082-1090).

Figure 4A:
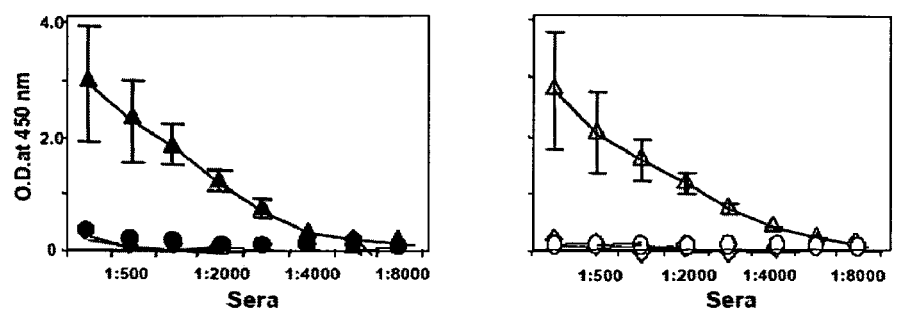
FIGS. 4A and 4B are graphical depictions of the immunogenicity of peptide PMK2-23H3 in BALB/c mice. Sera harvested before immunization (circle) and on days 7 (square) and 28 (triangle) after immunization from BALB/c mice immunized with anti-id mAb-derived peptide PMK2-23H3 were tested for their reactivity in ELISA with the immunizing peptide (closed symbols, left panel of FIG. 4A) and with HMW-MAA-derived peptide PHMW.D2.7 (open symbols, right panel of FIG. 4A). Sera harvested before immunization (circles) and on day 28 (triangles) were tested in ELISA (left panel in FIG. 4B) with HMW-MAA-transfected M14#5 cells (closed symbols) and with their mock-transfected counterparts (open symbols, left panel in FIG. 4B). Sera harvested on day 28 were tested by FACS analysis (right panel in FIG. 4B, open profiles) with HMW-MAA-transfected M14#5 cells (M14#5/HMW) and with their mock-transfected counterparts (M14#5/neo). Preimmune sera (filled profile) were used as controls.
Figure 4B:
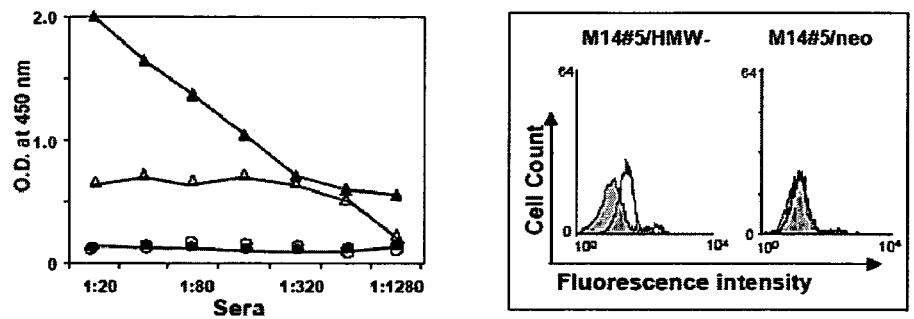

The results shown in FIGS. 4A and 4B demonstrate that anti-id mAb MK2-23H3-derived peptide PMK2-23H3 elicited in BALB/c mice antibodies that reacted with the immunizing peptide, with the HMW-MAA-derived peptide PHMW.D2.7 and with anti-id mAb MK2-23, as measured in a peptide binding assay (FIG. 4A). The elicited antibody response is specific, since the sera from the mice immunized with the irrelevant peptide Pb2m displayed no detectable reactivity with peptides PMK2-23H3 and PHMW.D2.7. Additionally, peptide PMK2-23H3 elicited in BALB/c mice antibodies with selective reactivity with HMW-MAA-bearing cells. As shown in FIG. 4B, sera from peptide PMK2-23H3-immunized mice reacted with HMW-MAA-transfected M14 melanoma cells (M14.HMW-MAA), but did not react with the mock-transfected counterpart (M14.neo) both in ELISA and in FACS analysis. Thus, PMK2-23H3 peptide can stimulate antibodies that recognize HMW-MAA. These results indicate that the peptide PMK2-23H3 can break unresponsiveness to a self-tumor antigen.

EXAMPLE 4

Figure 5:
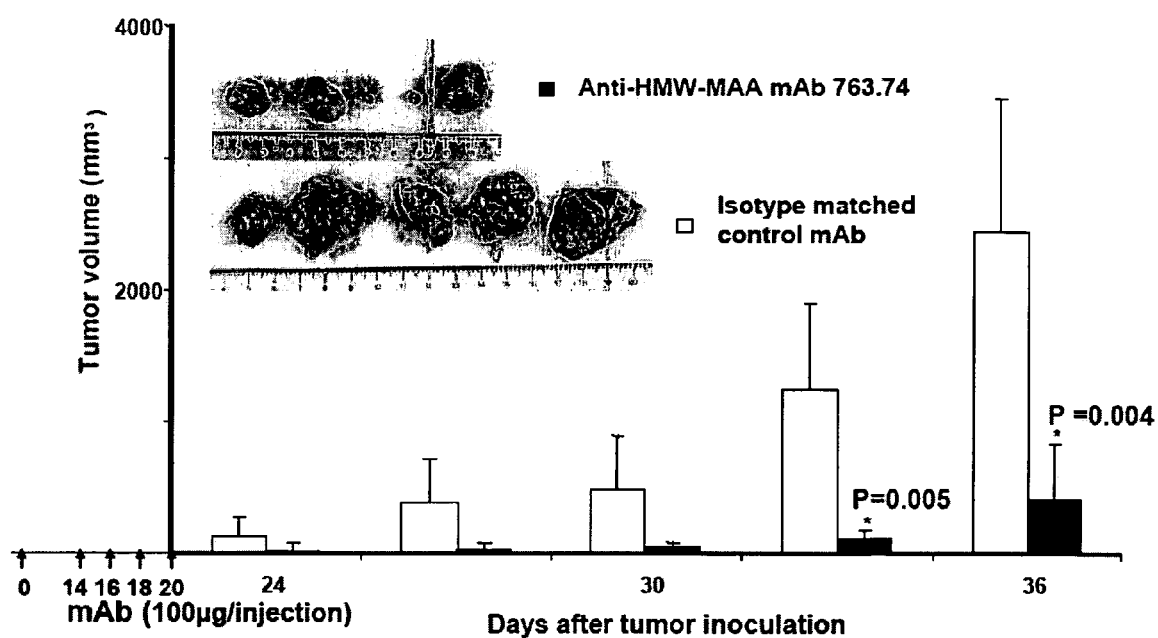
FIG. 5 is a graphical depiction and photographic representation of results from SCID mice injected with human melanoma Mv3 cells and subsequent treatment of tumor bearing mice with HMW-MAA-specific mAb 763.74 or an isotype matched irrelevant mAb.

This Example demonstrates that an antibody which binds to HMW-MAA can inhibit the in vivo growth of melanoma. To illustrate this, the HMW-MAA specific mAb 763.74 was used in SCID mice as follows. Human melanoma MV3 cells ($1 \times 10^6$) were injected subcutaneously into each of 10 SCID mice on day 0. On day 14, when tumor became palpable in every mouse, mice were divided randomly into two groups. Tumor-bearing mice (5/group) were injected intravenously with HMW-MAA-specific mAb 763.74 (100 µg/injection) on day 14, 16, 18 and 20 after tumor inoculation. Five mice were injected intravenously with an isotype matched irrelevant mAb which was used as a control. Tumor volumes were estimated by determining the maximum length (L) and perpendicular width (W) of each tumor and applying the formula volume=$\pi/6 \times L \times W^2$. The statistical significance of the difference between two groups was analyzed utilizing the two-tailed, unpaired Student's t test. The results are shown in FIG. 5 and demonstrate that administration of mAb 763.74 (against which anti-id mAb MK2-23 was raised) can inhibit the growth of melanoma cells in vivo. Thus, since the peptide PMK2-23H3 is able to elicit antibodies directed to the same epitope to which mAb 763.74 is directed, PMK2-23H3 (as well as PMK2-23L1 and PHMW-MAA.D2.7) can also be used for stimulating an immune response for inhibiting the growth of melanoma cells in vivo.

While this invention has been illustrated by specific embodiments, routine modifications will be apparent to those skilled in the art and such modifications are intended to be within the scope of the invention and the following claims.

The invention claimed is:

1. A composition comprising one or more peptides selected from the group consisting of peptides having the sequence of SEQ ID NO:1, SEQ ID NO:2 and SEQ ID NO:3, and wherein the peptide is capable of stimulating an antibody response against high molecular weight-melanoma associated antigen (HMW-MAA).

2. The composition of claim 1, wherein the peptide has the sequence of SEQ ID NO:1.

3. The composition of claim 1, wherein the peptide has the sequence of SEQ ID NO:2.

4. The composition of claim 1, wherein the peptide has the sequence of SEQ ID NO:3.

5. The composition of claim 1, wherein a peptide has the sequence of SEQ ID NO:1 and a peptide has the sequence of SEQ ID NO:2.

6. The composition of claim 1, further comprising a pharmaceutically acceptable carrier.

7. The composition of claim 6, further comprising an adjuvant.

8. The composition of claim 6, further comprising a cytokine.

9. A method for stimulating an immune response against HMW-MAA in an individual comprising administering to the individual an amount of a composition effective to elicit an immune response against HMW-MAA wherein the composition comprises one or more peptides selected from the group consisting of peptides having the sequence of SEQ ID NO:1, SEQ ID NO:2 and SEQ ID NO:3.

10. The method of claim 9, wherein the peptide has the sequence of SEQ ID NO:1.

11. The method of claim 9, wherein the peptide has the sequence of SEQ ID NO:2.

12. The method of claim 9, wherein the peptide has the sequence of SEQ ID NO:3.

13. The method of claim 9, wherein the composition further comprises a pharmaceutically acceptable carrier.

14. The method of claim 13, wherein the composition further comprises an adjuvant.

15. The composition of claim 13, wherein the composition further comprises a cytokine.

16. The method of claim 13, wherein the individual has a melanoma.

17. The method of claim 13, wherein the composition is administered by a route selected from intradermal, intramuscular, intraperitoneal, intravenous, subcutaneous, and intranasal.

18. The method of claim 13, wherein the composition comprises a peptide having the sequence of SEQ ID NO:1 and a peptide having the sequence of SEQ ID NO:2.

* * * * *

SEQUENCE LISTING

<160> NUMBER OF SEQ ID NOS: 7

<210> SEQ ID NO 1
<211> LENGTH: 15
<212> TYPE: PRT
<213> ORGANISM: mouse anti-Id mAb MK2-2
<220> FEATURE:
<223> OTHER INFORMATION: PMK2-23H3 peptide

<400> SEQUENCE: 1

Ala Arg Ser Asn Tyr Val Gly Tyr His Val Arg Trp Tyr Phe Asp
                 5                  10                  15

<210> SEQ ID NO 2
<211> LENGTH: 11
<212> TYPE: PRT
<213> ORGANISM: mouse anti-Id mAb MK2-2
<220> FEATURE:
<223> OTHER INFORMATION: PMK2-23L1 peptide

<400> SEQUENCE: 2

Ser Val Glu Tyr Tyr Gly Ser Ser Leu Met Gln
                 5                  10  11

<210> SEQ ID NO 3
<211> LENGTH: 17
<212> TYPE: PRT
<213> ORGANISM: human HMW-MAA protein
<220> FEATURE:
<223> OTHER INFORMATION: PHMW-MAA.D2.7 peptide

<400> SEQUENCE: 3

Ile Arg Ser Gly Asp Glu Val His Tyr His Val Thr Ala Gly Pro Arg Trp
                 5                  10                  15      17

<210> SEQ ID NO 4
<211> LENGTH: 12
<212> TYPE: PRT
<213> ORGANISM: human
<220> FEATURE:
<223> OTHER INFORMATION: Beta 2-microglobulin peptide

<400> SEQUENCE: 4

Lys Asn Gly Glu Arg Ile Glu Lys Val Glu His Ser
                 5                  10  12

<210> SEQ ID NO 5
<211> LENGTH: 15
<212> TYPE: PRT
<213> ORGANISM: mouse anti-Id mAb MK2-2
<220> FEATURE:
<223> OTHER INFORMATION: anti-id mAb MK2-23 L1 loop sequence

<400> SEQUENCE: 5

Arg Ala Ser Glu Ser Val Glu Tyr Tyr Gly Ser Ser Leu Met Gln
                 5                  10                  15

<210> SEQ ID NO 6
<211> LENGTH: 14
<212> TYPE: PRT
<213> ORGANISM: mouse anti-Id mAb MK2-2
<220> FEATURE:
<223> OTHER INFORMATION: anti-id mAb MK2-23 H3 loop sequence

<400> SEQUENCE: 6

```
Ser Asn Tyr Val Gly Tyr His Val Arg Trp Tyr Phe Asp Val
                5               10              14

<210> SEQ ID NO 7
<211> LENGTH: 56
<212> TYPE: PRT
<213> ORGANISM: human HMW-MAA protein
<220> FEATURE:
<223> OTHER INFORMATION: partial human HMW-MAA protein sequence

<400> SEQUENCE: 7

Arg Val Ala Asn Gly Ser Ser Leu Val Val Pro Gln Gly Gly Gln
                5               10                      15

Gly Thr Ile Asp Thr Ala Val Leu His Leu Asp Thr Asn Leu Asp
                20              25                      30

Ile Arg Ser Gly Asp Glu Val His Tyr His Val Thr Ala Gly Pro
                35              40                      45

Arg Trp Gly Gln Leu Val Arg Ala Gly Gln Pro
```